(12) United States Patent
Inoue et al.

(10) Patent No.: US 10,390,723 B2
(45) Date of Patent: Aug. 27, 2019

(54) RISE ACTION ASSISTANCE DEVICE AND RISE ACTION ASSISTANCE METHOD

(71) Applicant: Panasonic Intellectual Property Management Co., Ltd., Osaka (JP)

(72) Inventors: Tsuyoshi Inoue, Nara (JP); Hiroyuki Motoyama, Osaka (JP); Yusuke Kato, Nara (JP); Jun Ozawa, Nara (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 349 days.

(21) Appl. No.: 15/431,774

(22) Filed: Feb. 14, 2017

(65) Prior Publication Data
US 2017/0258359 A1 Sep. 14, 2017

(30) Foreign Application Priority Data

Mar. 9, 2016 (JP) .................................. 2016-045263

(51) Int. Cl.
*A61B 5/0488* (2006.01)
*A61B 5/04* (2006.01)
(Continued)

(52) U.S. Cl.
CPC ...... *A61B 5/04888* (2013.01); *A61B 5/04012* (2013.01); *A61B 5/0488* (2013.01); *A61B 5/1071* (2013.01); *A61B 5/1116* (2013.01); *A61B 5/1121* (2013.01); *A61B 5/4585* (2013.01); *A61B 5/6828* (2013.01); *A61G 5/14* (2013.01); *A61H 1/024* (2013.01); *A61H 3/00* (2013.01); *A61H 2003/007* (2013.01); *A61H 2201/1207* (2013.01);
(Continued)

(58) Field of Classification Search
CPC . A61B 5/04888; A61B 5/1071; A61B 5/1116; A61B 5/6828; A61G 5/14; A61H 1/024; A61H 2230/605; A61H 3/00
See application file for complete search history.

(56) References Cited

U.S. PATENT DOCUMENTS

2007/0256494 A1   11/2007   Nakamura et al.
2008/0234608 A1*   9/2008   Sankai ............... A61B 5/04888
                                                         601/5

FOREIGN PATENT DOCUMENTS

JP    2004-194780    7/2004
JP    2004-275214    10/2004
(Continued)

*Primary Examiner* — Brian A Dukert
(74) *Attorney, Agent, or Firm* — Wenderoth, Lind & Ponack, L.L.P.

(57) ABSTRACT

A rise action assistance device according to an aspect of the present disclosure is provided with: a myoelectric potential acquirer that acquires a myoelectric value of a sitting user's tibialis anterior muscle, and a myoelectric value of the sitting user's vastus lateralis muscle or a myoelectric value of the sitting user's vastus medialis muscle; an angle acquirer that acquires a bend angle of the sitting user's upper body; a detector circuit that detects a start of a rise action by the user, based on the myoelectric value of the user's tibialis anterior muscle, the myoelectric value of the user's vastus lateralis muscle or the myoelectric value of the user's vastus medialis muscle, and the bend angle of the user's upper body; and an assistor that starts assistance of the rise action after the start of the rise action is detected.

6 Claims, 12 Drawing Sheets

(51) Int. Cl.
- *A61B 5/11* (2006.01)
- *A61G 5/14* (2006.01)
- *A61H 3/00* (2006.01)
- *A61B 5/00* (2006.01)
- *A61H 1/02* (2006.01)
- *A61B 5/107* (2006.01)

(52) U.S. Cl.
CPC .......... *A61H 2201/165* (2013.01); *A61H 2201/5007* (2013.01); *A61H 2201/5069* (2013.01); *A61H 2201/5079* (2013.01); *A61H 2201/5097* (2013.01); *A61H 2205/102* (2013.01); *A61H 2230/605* (2013.01)

(56) References Cited

FOREIGN PATENT DOCUMENTS

| | | |
|---|---|---|
| JP | 2013-158346 | 8/2013 |
| JP | 2014-236786 | 12/2014 |

* cited by examiner

FIG. 12

| TEST PARTICIPANT | TIME UNTIL SEAT SEPARATION | | |
|---|---|---|---|
| | TA | VM | VL |
| PIN1 | 410.2 | 84.2 | 102.1 |
| PIN2 | 593.5 | 72.4 | 123.8 |
| PIN3 | 116.3 | 66.1 | 76.7 |
| PIN4 | 402.5 | 94.1 | 142.6 |
| PIN5 | 301.1 | 190.6 | 202.4 |
| MEAN | 364.7 | 101.48 | 129.52 |

FIG. 13

| TEST PARTICIPANT | TIME UNTIL SEAT SEPARATION |
|---|---|
| PIN1 | 84.2 |
| PIN2 | 72.4 |
| PIN3 | 63.8 |
| PIN4 | 94.1 |
| PIN5 | 190.6 |
| ALL | 101.4 |

RISE ACTION ASSISTANCE DEVICE AND RISE ACTION ASSISTANCE METHOD

BACKGROUND

1. Technical Field

The present disclosure relates to technology that assists with a rise action of a user.

2. Description of the Related Art

Japanese Unexamined Patent Application Publication No. 2013-158346 discloses a walking assistance device. The walking assistance device described in Japanese Unexamined Patent Application Publication No. 2013-158346 determines whether or not a user's knee is in an extended state, based on the load on the sole of the user's foot, the orientation of the user's foot, and the load torque on a driving means of the user.

The walking assistance device in Japanese Unexamined Patent Application Publication No. 2013-158346 detects the extended state by using the orientation of the foot and the load on the sole. However, detecting the intent to perform a rise action as quickly as possible, and assisting the action at a timing suited to the rise action, are not disclosed.

SUMMARY OF THE INVENTION

In one general aspect, the techniques disclosed here feature a rise action assistance device including: a myoelectric potential acquirer that acquires a myoelectric value of a sitting user's tibialis anterior muscle, and at least one of a myoelectric value of the sitting user's vastus lateralis muscle and a myoelectric value of the sitting user's vastus medialis muscle; an angle acquirer that acquires a bend angle of the sitting user's upper body; a detector circuit that detects a start of a rise action by the user, based on the myoelectric value of the user's tibialis anterior muscle, at least one of the myoelectric value of the user's vastus lateralis muscle and the myoelectric value of the user's vastus medialis muscle, and the bend angle of the user's upper body; and an assistor that starts assistance of the rise action after the detector circuit detects the start of the rise action. The detector circuit detects that the sitting user has started the rise action when (a) the myoelectric value of the user's tibialis anterior muscle acquired by the myoelectric potential acquirer within a first certain amount of time is equal to or greater than a first threshold value, (b) at least one of the myoelectric value of the user's vastus lateralis muscle and the myoelectric value of the user's vastus medialis muscle acquired by the myoelectric potential acquirer within the first certain amount of time is equal to or greater than a second threshold value, and (c) the bend angle of the user's upper body acquired by the angle acquirer within the first certain amount of time is increasing.

It should be noted that these general or specific aspects may also be realized by a system, method, integrated circuit, computer program, or computer-readable recording medium, and may also be realized by an arbitrary combination of a system, method, integrated circuit, computer program, and recording medium. Computer-readable recording media include non-volatile recording media such as Compact Disc—Read-Only Memory (CD-ROM), for example.

According to the present disclosure, it is possible to detect the intent to perform a rise action as quickly as possible, and assist the action at a timing suited to the rise action.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 12 is a diagram illustrating test results of the amount of time from the start time of muscle activity until the start of rising;

FIG. 13 is a diagram illustrating test results of the amount of time from the rise action detection time until the seat separation time;

DETAILED DESCRIPTION (Underlying Knowledge Forming Basis of the Present Disclosure)

When assistance with a rise action is started after a user starts a rise action, the timing of the assistance may be too late in some cases. In Japanese Unexamined Patent Application Publication No. 2013-158346, walking assistance is provided by sensing an extended state. In other words, walking assistance starts after sensing that walking has started.

A rise action, which is included in various actions by a person, demands that the person shift his or her center of gravity greatly, and also use a large amount of force. For example, a person starts a rise action after finishing preparations for the rise action, such as shifting his or her center of gravity before performing the rise action. For example, by beginning the assistance of the rise action after the preparations are finished, there is a possibility of inducing in the person a sense of unnaturalness or discomfort with respect to the rise action.

Accordingly, the inventors realized that to assist with the rise action of a seated person, it is necessary to detect the intent to perform the rise action before the rise action is started.

Taking the detection of the intent to perform a rise action as an objective, the inventors discovered that from among various information for acquiring the preparations of a rise action by a person, it is possible to detect the intent to perform a rise action before the rise action is started, according to the myoelectric potential of a person's lower limbs and the torso angle. Hereinafter, the results of a test carried out by the inventors to obtain this knowledge will be illustrated.

The test participants where five adult males, aged 32.4±6.7 (mean value±standard deviation), with a height of 169.3±9.0 cm, and a weight of 62.2±7.0 kg. The test participants did not have a medical history that would affect rising and sitting actions.

Figure 10:
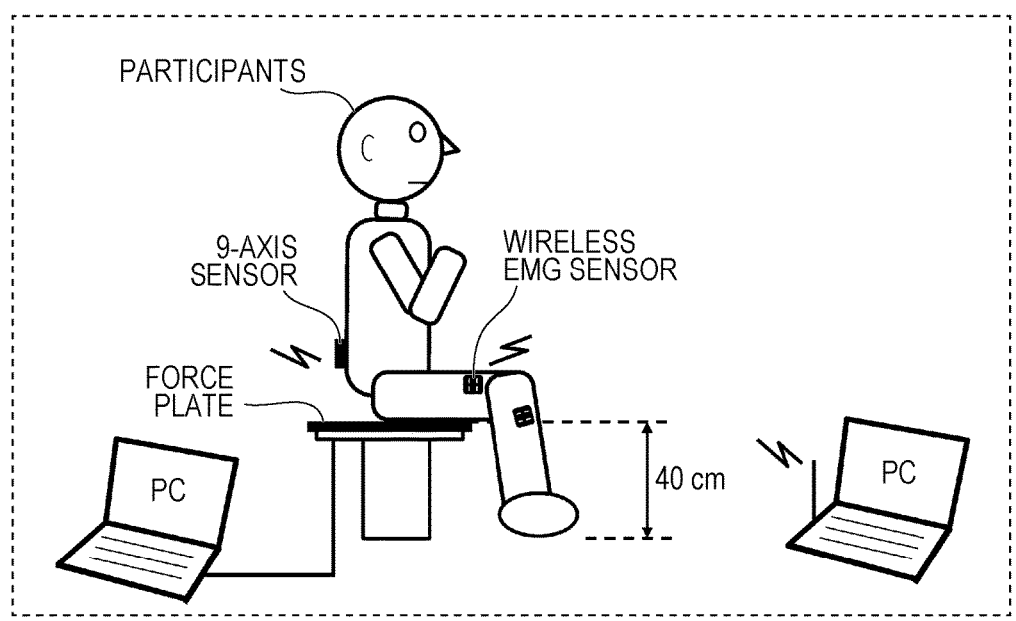
FIG. 10 is a diagram illustrating a test environment.

FIG. 10 illustrates the test environment. The test participants wore myoelectric sensors at three sites on the lower limbs. For the myoelectric sensors, wireless EMG sensors (Trigno, manufactured by Delsys) were used. Specifically, the myoelectric sensors were worn at the rectus femoris muscle (RF), the vastus medialis muscle (VM), and the vastus lateralis muscle (VL) of the right lower limb. Additionally, the test participants wore a torso angle sensor on the lower back. For the torso angle sensor, a 9-axis wireless motion sensor (IMU-Z2, manufactured by ZMP) was used. Additionally, to measure the timing at which the buttocks separate from the seat of the chair (seat separation), a floor reaction force measurement device (TF-3040, manufactured by Tec Gihan) was installed in the seat of the chair.

The test participants were instructed to repeatedly perform a rise action of rising from the chair and a sit action of sitting in the chair on a fixed time interval. The test participants performed the rise and sit actions (20 times each). During the actions, the myoelectric potential of the lower limbs was measured by the myoelectric sensors, and the torso angle was measured by the torso angle sensor. The rise action of rising from the chair and the sit action of sitting in the chair were performed with arms folded, thereby reducing the influence of the upper limbs of the test participants. Also, the test participants were instructed not to move the position of their feet during the rise actions and sit actions. The feet position was decided prior to the test, at a position enabling the rise actions and the sit actions to be performed without requiring excessive force.

Figure 11A:
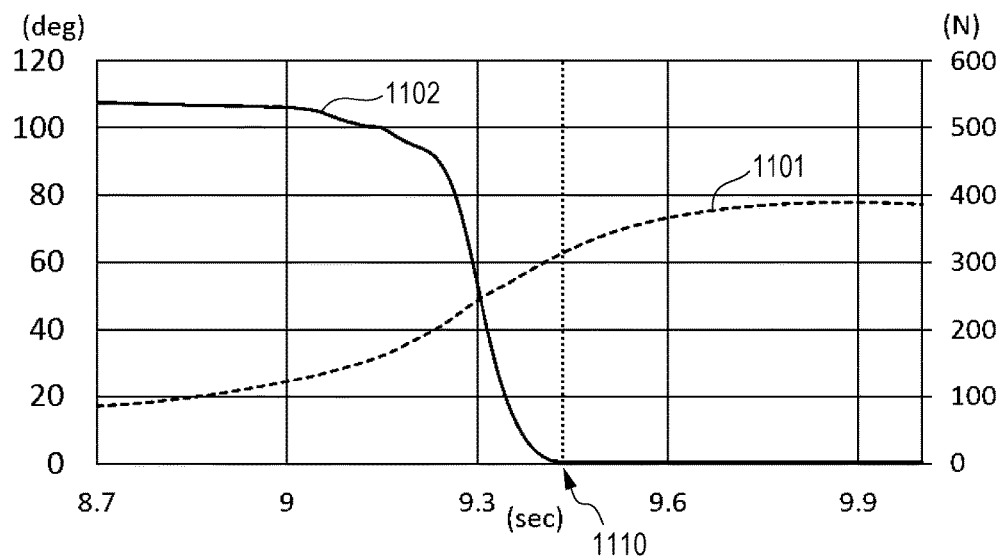
FIG. 11A is a diagram illustrating an example of measurement results of torso bend angle and floor reaction force.
Figure 11B:
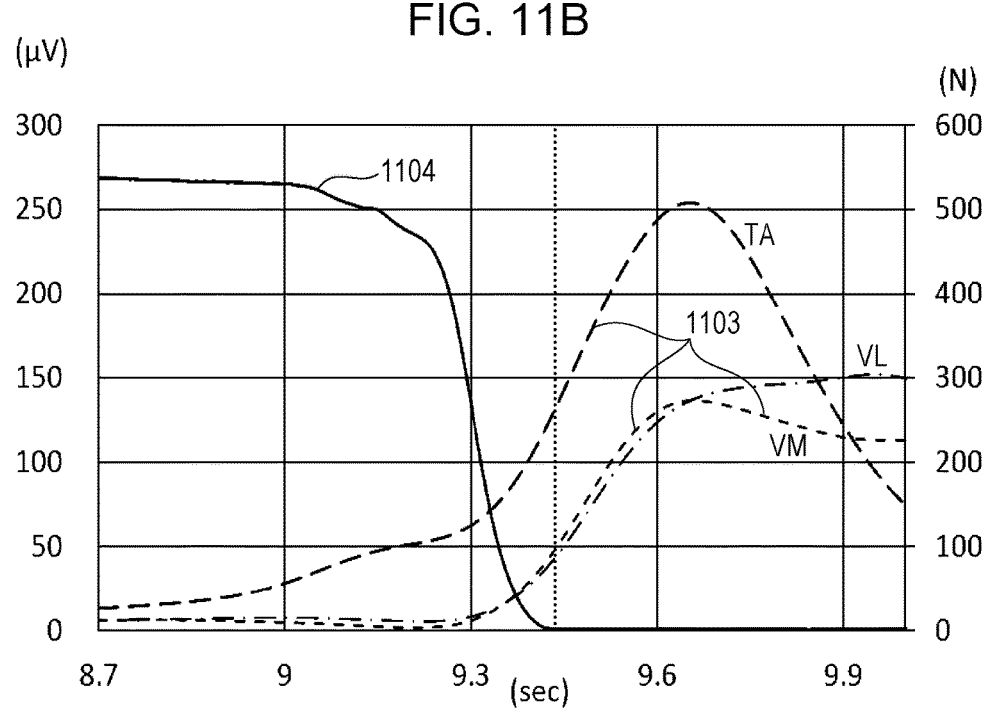
FIG. 11B is a diagram illustrating an example of measurement results of myoelectric potential and floor reaction force.

FIGS. 11A and 11B illustrate the measurement results of the torso angle, myoelectric potential, and floor reaction force. FIG. 11A illustrates the measurement results of the torso bend angle 1011 (deg) and the floor reaction force 1102 (N). FIG. 11B illustrates the measurement results of the myoelectric potential 1103 (μV) and the floor reaction force 1104 (N). Note that the myoelectric potential 1103 illustrated in FIG. 11B is not the measurement value, but instead the value obtained by applying full-wave rectification and a 3 Hz low-pass filter to the measurement value (myoelectric waveform). The timing 1110 illustrated in FIG. 11A means the time point at which the buttocks of the test participant separated from the chair.

In addition, the torso angle 1101 illustrated in FIG. 11A is the angle of the torso with respect to the vertical direction. The torso angle 1101 is a value that increases as a test participant bends forward. The torso bend angle 1101 increases before seat separation at which the measurement result of the floor reaction force 1102 becomes 0 N, as illustrated in FIG. 11A, and the magnitude of the myoelectric potential 1103 also increases, as illustrated in FIG. 11B.

FIG. 12 illustrates, for each test participant, the amount of time (ms) from the time at which the myoelectric potential is equal to or greater than a threshold value until the time at which the measurement value of the floor reaction force is less than or equal to a threshold value. As illustrated in FIG. 12, the data for all test participants demonstrates that activity in the tibialis anterior muscle (TA), the vastus medialis muscle (VM), and the vastus lateralis muscle (VL) occurs before seat separation. Also, as illustrated in FIG. 12, the data for all test participants demonstrates that the tibialis anterior muscle (TA) is active earlier than the vastus medialis muscle (VM) and the vastus lateralis muscle (VL).

Accordingly, the method discussed in the following embodiment was used on the measurement results for each test participant to detect the intent to perform a rise action, and compute the amount of time from the time at which the intent was detected until the time of seat separation. FIG. 13 illustrates the test results. According to FIG. 13, for all test participants, the rise action was successfully detected before seat separation. In other words, according to the knowledge obtained by the test carried out by the inventors, it is apparent that the intent to perform a rise action may be detected before the rise action is started. Particularly, the inventors discovered new knowledge that by using myoelectric potential information and preparation information for a rise action (forward bend posture), it is possible to distinguish from information about actions other than a rise action, and detect the intent to start a rise action before the rise action is started. Based on this knowledge, the inventors devised a rise action assistance device and a rise action assistance method according to the present disclosure.

(Embodiment 1)

Figure 1:
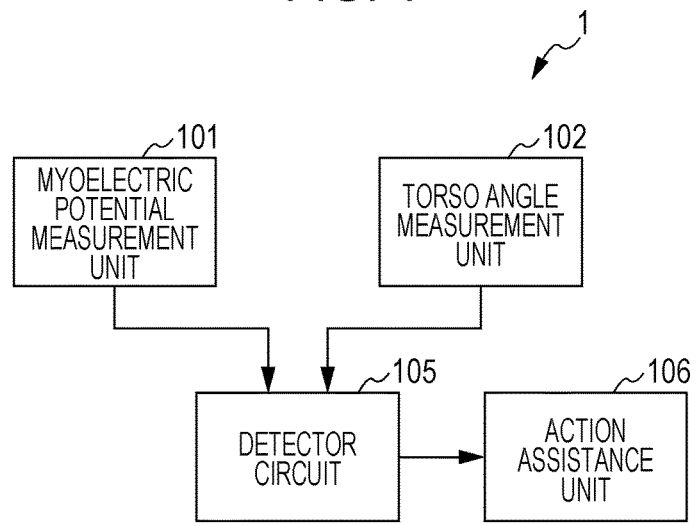
FIG. 1 is a diagram illustrating function blocks of a rise action assistance device.

FIG. 1 illustrates a function block diagram of a rise action assistance device 1 according to an aspect of the present disclosure. The rise action assistance device 1 illustrated in FIG. 1 is equipped with a myoelectric potential measurement unit 101, a torso angle measurement unit 102, a detector circuit 105, and an action assistance unit 106.

Figure 2:
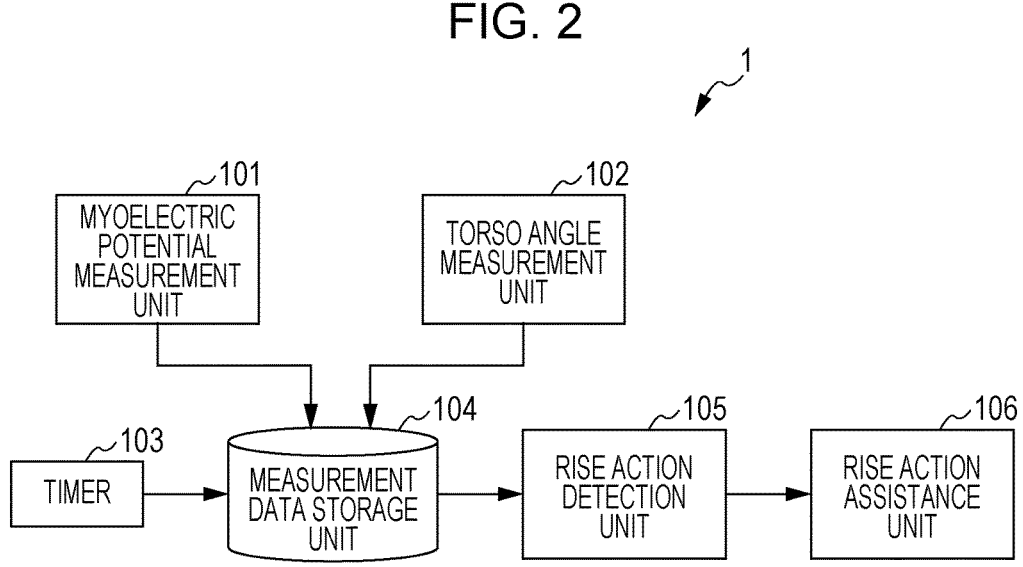
FIG. 2 is a diagram illustrating function blocks of a rise action assistance device.

FIG. 2 illustrates another example of the rise action assistance device 1. In addition to the rise action assistance device 1 illustrated in FIG. 1, a timer 103 and a storage unit 104 may also be provided. Note that the rise action detection unit in FIG. 2 corresponds to the detector circuit in FIG. 1, and the rise action assistance unit in FIG. 2 corresponds to the action assistance unit in FIG. 1. Hereinafter, each of these structural elements will be described.

(Myoelectric Potential Measurement Unit 101)

The myoelectric potential measurement unit 101 uses electrodes placed on the user's lower limbs to acquire a myoelectric value of the user's lower limbs. The myoelectric value of the user's lower limbs includes a myoelectric value of the tibialis anterior muscle, a myoelectric value of the vastus lateralis muscle, or a myoelectric value of the vastus medialis muscle. Herein, myoelectric values encompass both measured values and values computed from measured values. Note that it is sufficient for the myoelectric potential measurement unit 101 to acquire at least one of the myoelectric value of the vastus lateralis muscle and the myoelectric value of the vastus medialis muscle.

Figure 3:
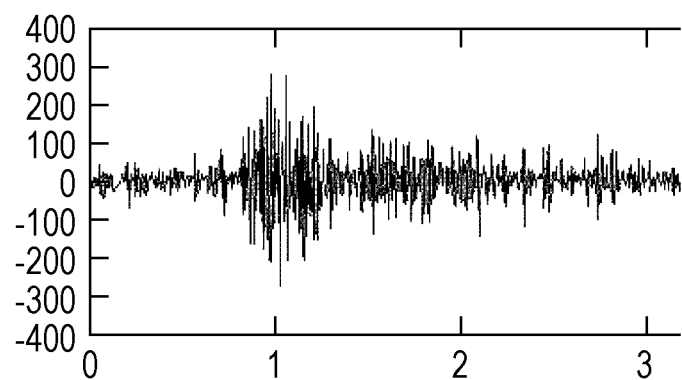
FIG. 3 is a diagram illustrating an example of a myoelectric waveform.

Specifically, the myoelectric potential measurement unit 101 acquires a myoelectric waveform of the user's lower limbs. FIG. 3 illustrates an example of a myoelectric waveform. In the myoelectric waveform, the vertical axis represents the measurement value of the myoelectric potential (V), and the horizontal axis represents time (s).

Figure 15:
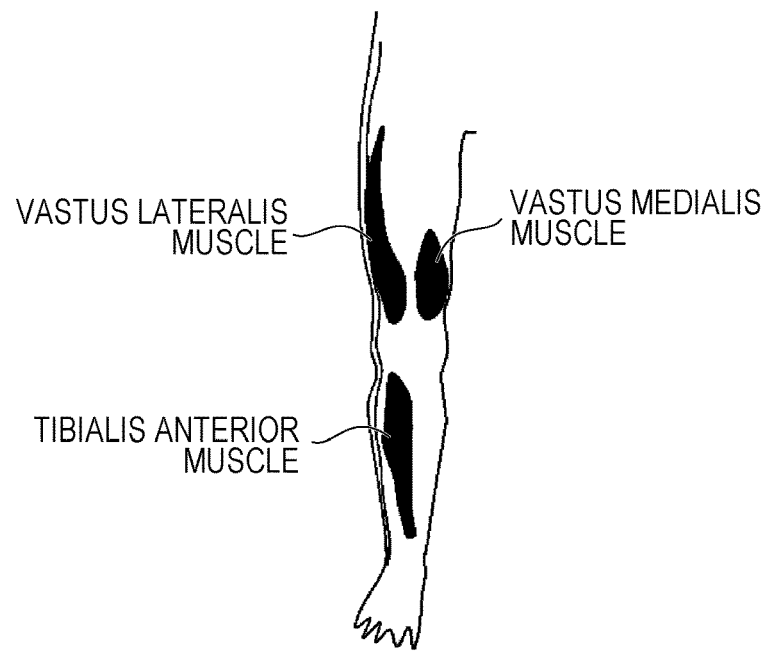
FIG. 15 is a diagram illustrating the positions of the tibialis anterior muscle, the vastus lateralis muscle, and the vastus medialis muscle.

An example of the hardware of the myoelectric potential measurement unit 101 is a myoelectric sensor 1011. For example, the myoelectric sensor 1011 includes multiple electrodes 1012 and a myoelectric measurement circuit 1013. The electrodes 1012 are respectively placed on the user's skin over the tibialis anterior muscle, and the skin over the vastus lateralis muscle or vastus medialis muscle. FIG. 15 illustrates the positions of the tibialis anterior muscle, the vastus lateralis muscle, and the vastus medialis muscle. The myoelectric measurement circuit 1013 uses the multiple electrodes to measure the myoelectric potential of the user's lower limbs.

The myoelectric sensor 1011 may also include an amplifier 1014. The myoelectric sensor 1011 uses the amplifier 1014 to amplify the value of the electric potential measured using the multiple electrodes, and the amplified values may be acquired as measurement values of the user's myoelectric potential.

An example of the amplifier 1014 is a differential amplifier circuit. By the amplifier 1014, the differential voltage between an electric potential (V1) measured using the electrode 1011a and an electric potential (V2) measured using the electrode 1012b is amplified.

Figure 4:
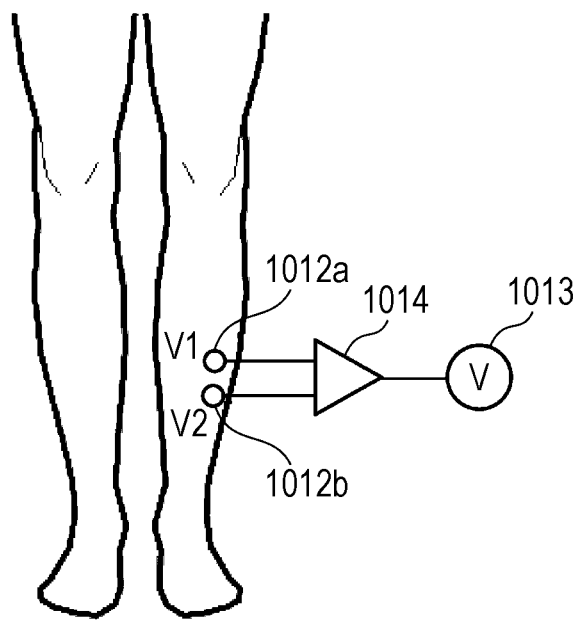
FIG. 4 is a diagram illustrating an example of a myoelectric sensor.

FIG. 4 illustrates an example of the myoelectric sensor 1011. The myoelectric sensor 1011 illustrated in FIG. 4 includes multiple electrodes 1012a and 1012b, an amplifier 1014, and a myoelectric measurement circuit 1013.

The electrodes 1012a and 1012b are placed on the user's skin over the tibialis anterior muscle. For example, there is from 10 mm to 30 mm between the electrode 1012a and the electrode 1012b. The myoelectric measurement circuit 1013 measures the electric potential difference between earth and the electrode 1012a, and also between earth and the electrode 1012b.

The myoelectric potential measurement unit 101 may also acquire the time of measuring the user's myoelectric potential from a timer 103, and store the measurement value of the myoelectric potential of the user's lower limbs in association with the measurement time in the storage unit 104.

The myoelectric potential measurement unit 101 may also measure the user's myoelectric potential on a first time interval, and store in the storage unit 104 the measurement values of the user's myoelectric potential in the order in which the values are measured.

(Activity Value of Tibialis Anterior Muscle)

Figure 5A:
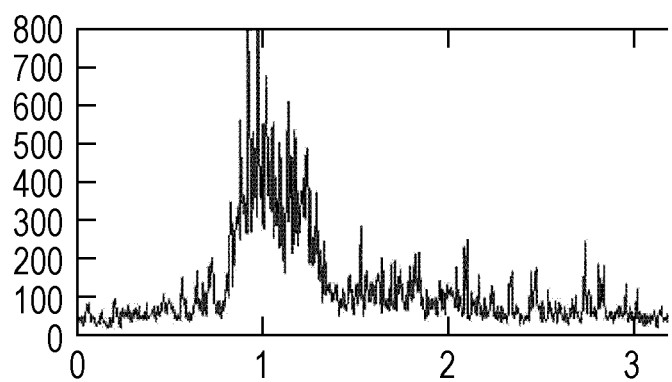
FIG. 5A is a diagram illustrating a step of acquiring an activity value of the tibialis anterior muscle from a measurement value of the tibialis anterior muscle.
Figure 5B:
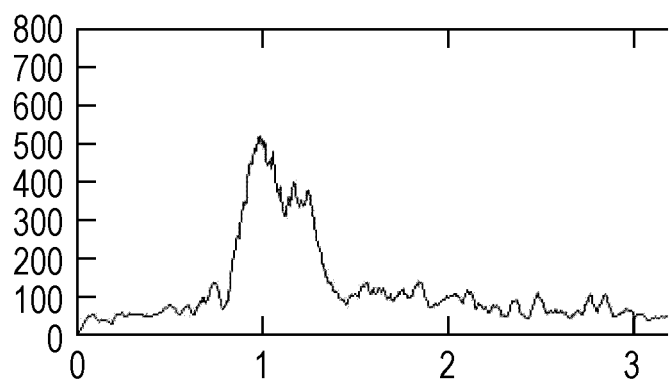
FIG. 5B is a diagram illustrating a step of acquiring an activity value of the tibialis anterior muscle from a measurement value of the tibialis anterior muscle.

FIGS. 5A and 5B illustrate a step of acquiring an activity value of the tibialis anterior muscle from a measurement value of the tibialis anterior muscle. As illustrated in FIG. 5A, the myoelectric measurement circuit 1013 applies full-wave rectification to the myoelectric waveform of the tibialis anterior muscle illustrated in FIG. 3.

As illustrated in FIG. 5B, a computational circuit acquires a waveform having a certain frequency from among the full-wave rectified waveform. The computational circuit uses a low-pass filter, for example, to acquire a waveform having a frequency from 2 Hz to 5 Hz. This waveform also expresses an activity waveform of the tibialis anterior muscle. The values at each of the times included in the activity waveform of the tibialis anterior muscle express the activity values of the tibialis anterior muscle. As above, the myoelectric potential measurement unit 101 may also acquire an activity value of the tibialis anterior muscle as the myoelectric value of the tibialis anterior muscle.

(Activity Value of Vastus Lateralis Muscle or Vastus Medialis Muscle)

The myoelectric measurement circuit 1013 acquires an activity value of the vastus lateralis muscle or the vastus medialis muscle, similar to the activity value of the tibialis anterior muscle. In the example illustrated in FIGS. 5A and 5B, the case of the tibialis anterior muscle is described, but the myoelectric measurement circuit 1013 and the computational circuit are also able to acquire the activity values of other muscles similarly. For example, in the case of the vastus lateralis muscle or the vastus medialis muscle, the myoelectric measurement circuit 1013 likewise applies full-wave rectification to the acquired myoelectric waveform of the vastus medialis muscle and the vastus medialis muscle.

The computational circuit acquires a waveform having a certain frequency from among the full-wave rectified waveform. The computational circuit uses a low-pass filter, for example, to acquire a waveform having a frequency from 2 Hz to 5 Hz. This waveform also expresses an activity waveform of the myoelectric potential (vastus lateralis muscle or vastus medialis muscle). The values at each of the times included in the activity waveform of the vastus medialis muscle or the vastus lateralis muscle express the activity values of the vastus medialis muscle or the vastus lateralis muscle.

(Torso angle measurement unit 102)

The torso angle measurement unit 102 measures the torso angle of the user's upper body. Examples of the torso angle of the user's upper body are the angle between the user's upper body and the earth's axis, or the angle between the user's upper body and the horizontal plane. A specific example of the user's upper body is the user's spine.

An example of the specific hardware of the torso angle measurement unit 102 is a 9-axis sensor. A 9-axis sensor includes an acceleration sensor, an angular velocity sensor, and a geomagnetic sensor. These sensors include an acceleration measurement circuit, an angular velocity measurement circuit, and a geomagnetic measurement circuit, respectively. The angle of the torso with respect to the vertical direction is calculable by the 9-axis sensor as the torso angle. Also, even if only the angular velocity sensor of the 9-axis sensor is used, the torso angle may be calculated by measuring the integrated value of a calibration and a measurement result.

Figure 6A:
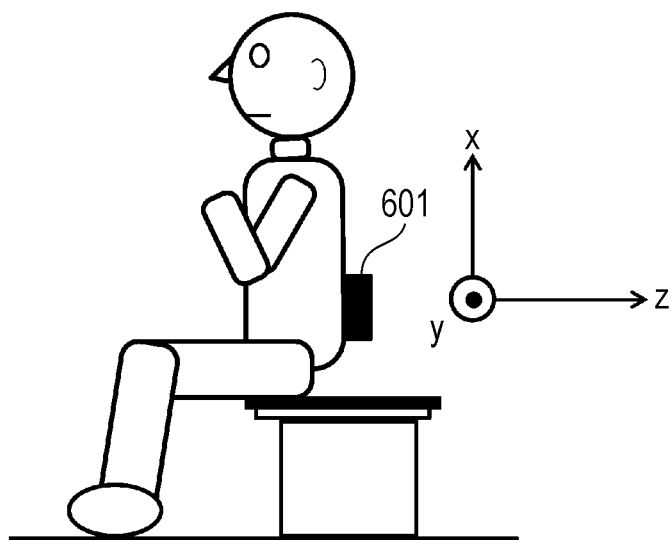
FIG. 6A is a diagram illustrating an example of wearing a torso angular velocity sensor.

FIG. 6A illustrates a torso angular velocity sensor 601 worn by the user. The torso angular velocity sensor 601 is placed on the lower back of a user sitting in a chair. As illustrated in FIG. 6A, an x-axis, y-axis, and z-axis are set.

Figure 6B:
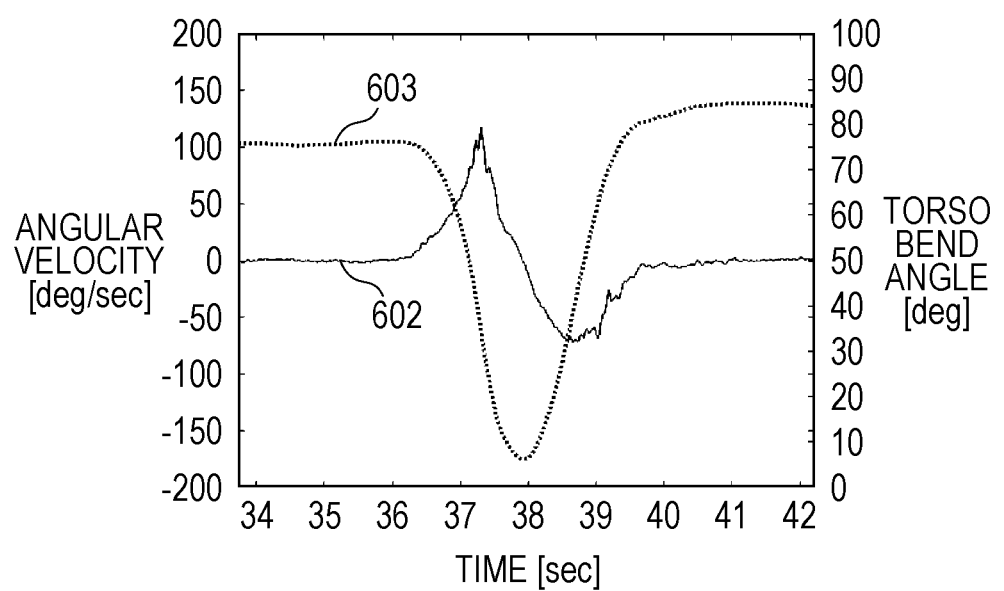
FIG. 6B is a diagram illustrating an example of torso angle measurement.

FIG. 6B illustrates a result of measuring the torso angle of the user's upper body with the torso angular velocity sensor illustrated in FIG. 6A. FIG. 6B illustrates a measurement value 602 of the angular velocity in the y-axis direction, and a torso angle 603 computed using the integrated value of the measurement value.

Note that the torso angular velocity measurement circuit and the torso angular velocity sensor acquire the torso angle based on changes of angle with respect to a reference angle. The reference angle may be set by calibration, or held in advance in internal memory included in the torso angle measurement unit 102. Also, the torso angle measurement unit 102 may use calibration to correct the reference angle held in advance. For example, the rise action assistance device 1 issues an instruction to position the torso angular velocity sensor in the x-axis direction, and the position of the torso angular velocity sensor after issuing the instruction is set as 90 degrees (reference position).

The torso angle measurement unit 102 may also acquire the time of measuring the user's torso from the timer 103, and store the measured angle of the user's torso in association with the measurement time in the storage unit 104.

The torso angle measurement unit 102 may also measure the torso angle of the user's upper body on a second time interval, and store in the storage unit 104 the torso angles of the user in the order in which the torso angles are measured. The first time interval and the second time interval may be different from each other, but preferably are the same.

(Storage Unit 104)

The storage unit 104 stores the myoelectric potential of the lower limbs and the torso angle of the upper body. For example, the myoelectric potential of the lower limbs and the torso angle of the upper body may be stored together with a user ID.

(Detector Circuit 105)

The detector circuit 105 detects the start of a rise action by the user, based on the myoelectric potential of the user's tibialis anterior muscle, the myoelectric potential of the user's vastus lateralis muscle or vastus medialis muscle, and the bend angle of the user's upper body.

Specifically, after a certain amount of time, the detector circuit 105 detects that a rise action by the user has started. In other words, the detector circuit 105 detects a state from the start timing of the rise action by the user, before the certain amount of time. An example of the certain amount of time is from 50 ms to 200 ms.

The rise action by the user means an action of a sitting user rising to stand up. An example of a rise action is the buttocks of a user sitting on a chair, the ground, or the like separating from the seat of the chair or the ground. An example of the start timing of a rise action is the time point at which the user's buttocks separates from the seat of the chair or the ground. In other words, the detector circuit 105 detects a state from the time point at which the user's buttocks separates from the seat of the chair or the ground, before the certain amount of time.

Note that the detector circuit 105 uses at least one of the myoelectric potential of the user's vastus lateralis muscle and vastus medialis muscle to detect the start of the rise action by the user.

The detector circuit 105 may also acquire, from the storage unit 104, information about the respective measurement times of the myoelectric potential of the user's tibialis anterior muscle and the myoelectric potential of the user's vastus lateralis muscle or vastus medialis muscle.

Alternatively, the detector circuit 105 may acquire, from the myoelectric potential measurement unit 101 and the torso angle measurement unit 102, the myoelectric potential of the user's tibialis anterior muscle, the myoelectric potential of the user's vastus lateralis muscle or vastus medialis muscle, and the bend angle of the user's upper body. At this point, the detector circuit 105 may also acquire the measurement times of the myoelectric potential from the myoelectric potential measurement unit 101 and the torso angle measurement unit 102. Alternatively, the detector circuit 105 may store the first time interval and the second time interval in internal memory, and for each of the myoelectric potential of the user's tibialis anterior muscle, the myoelectric potential of the user's vastus lateralis muscle or vastus medialis muscle, and the bend angle of the user's upper body, may use the order in which measurement values are received, the first time interval, and the second time interval to compute the measurement values and the measurement times. An example in which measurement values and measurement times are computed is (1st received measurement value, reference time), (2nd received measurement value, reference time+first time interval), (3rd received measurement time, reference time+first time interval×2), (nth received measurement value, reference time+first time interval×(n−1)) (where n is a natural number).

The detector circuit 105 identifies the start of a rise action by the user, based on a myoelectric value of the tibialis anterior muscle, a myoelectric value of the vastus lateralis muscle or a myoelectric value of the vastus medialis muscle, and a torso angle of the user's upper body.

More specifically, the detector circuit 105 identifies that the user has started a rise action when (a) the myoelectric value of the user's tibialis anterior muscle is equal to or greater than a first threshold value, (b), the myoelectric value of the user's vastus lateralis muscle or vastus medialis muscle is equal to or greater than a second threshold value, and (c) the bend angle of the user's upper body is increasing.

(Action Assistance Unit 106)

The action assistance unit 106 assists with a rise action, based on the start of the rise action detected by the detector circuit 105. Since the state from the start timing of the rise action by the user before the certain amount of time is detected by the detector circuit 105, it is desirable to start rise action assistance before the start of the rise action.

Figure 7:
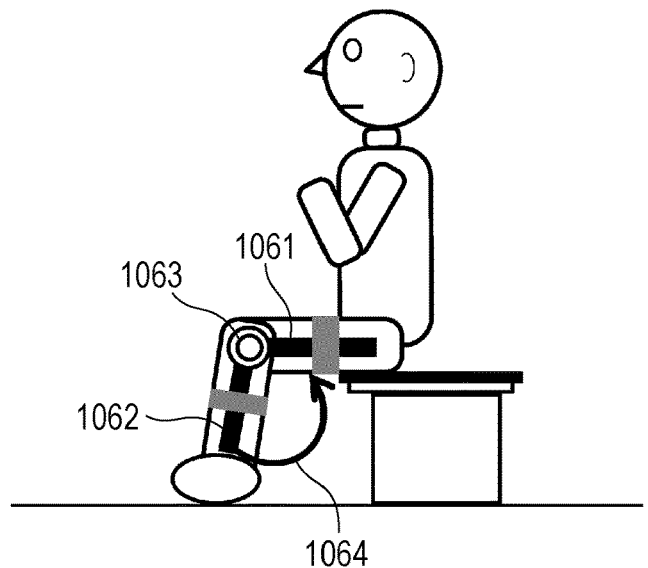
FIG. 7 is a diagram illustrating an example of an action assistance unit.

An example of the action assistance unit 106 is a robot or an assist suit worn on the user's lower limbs. FIG. 7 illustrates a specific example of the action assistance unit 106. The action assistance unit 106 illustrated in FIG. 7 includes an upper skeleton unit 1061, a lower skeleton unit 1062, and a power unit 1063. The upper skeleton unit 1061 and the lower skeleton unit 1062 are connected. Alternatively, the upper skeleton unit 1061 and the lower skeleton unit 1062 may be unified and able to change shape between the upper skeleton unit 1061 and the lower skeleton unit 1062. Hereinafter, a specific description will be given.

The upper skeleton unit 1061 is affixed to the thighs of the user's lower limbs. The lower skeleton unit 1062 is affixed to the feet or the lower legs of the user's lower limbs. The upper skeleton unit 1061 and the lower skeleton unit 1062 include respective brace harnesses, and are affixed to the user by the brace harnesses. Examples of brace harnesses are tape (a hook and loop fastener) or a belt. The brace harnesses may also be like laces. An example of the power unit 1063 includes a motor and an electrical power source.

Herein, the thighs refer to the portion of the legs above the knees. The lower legs refer to the portion of the legs below the knees, from the knees to the ankles.

As illustrated in FIG. 7, the power unit 1063 moves the upper skeleton unit 1061 in the direction in which the user extends his or her knees (the direction of the arrow 1064 in FIG. 7), centered between the upper skeleton unit 1061 and the lower skeleton unit 1062 (or the user's knees). The direction in which the user extends his or her knees refers to the direction in which the upper skeleton unit 1061 moves from a state in which the user's knees are bent to a state in which the knees are extended. Consequently, the action of the user standing up may be assisted.

Note that in the case in which the action assistance unit 106 is a fabric-type assist suit worn by the user, the upper skeleton unit 1061 and the lower skeleton unit 1062 may also be incorporated into the fabric.

(Process of Rise Action Assistance Device 1)

Figure 8:
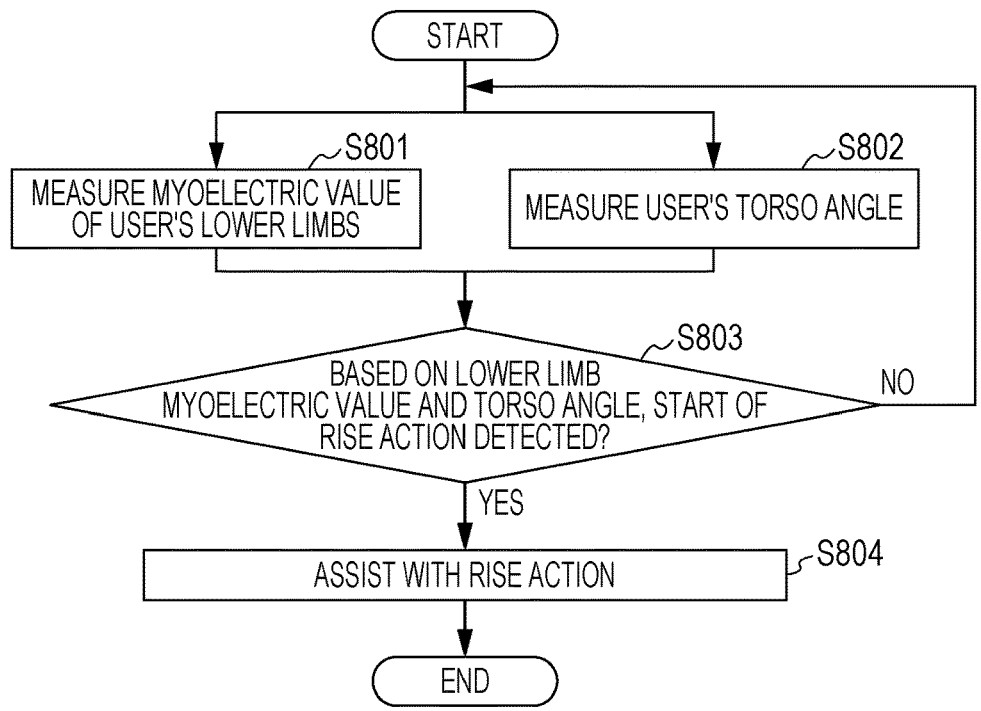
FIG. 8 is a diagram illustrating a flowchart of a process of a rise action assistance device.

FIG. 8 illustrates a flowchart of a process of the rise action assistance device 1.

(Step S801)

The myoelectric potential measurement unit 101 measures the myoelectric potential of the user's lower limbs, and obtains measurement values of the myoelectric potential of the user's lower limbs. The measurement values of the user's myoelectric potential includes a measurement value of the tibialis anterior muscle and a measurement value of the vastus lateralis muscle or a measurement value of the vastus medialis muscle.

For example, the myoelectric potential measurement unit 101 uses the measurement value of the tibialis anterior muscle to compute and acquire an activity value of the tibialis anterior muscle as a myoelectric value of the tibialis anterior muscle. The myoelectric potential measurement unit 101 uses the measurement value of the vastus lateralis muscle or the measurement value of the vastus medialis muscle to compute and acquire an activity value of the vastus lateralis muscle or the vastus medialis muscle as a myoelectric value of the vastus lateralis muscle or the vastus medialis muscle.

(Step S802)

The torso angle measurement unit 102 acquires the torso angle of the user.

(Step S803)

The detector circuit 105 detects whether or not a rise action has started, based on the myoelectric value of the tibialis anterior muscle, the myoelectric value of the vastus lateralis muscle or the vastus medialis muscle, and the torso angle. If the detector circuit 105 detects the start of a rise action, the process proceeds to step S804. If the detector circuit 105 does not detect the start of a rise action, the process returns to the start.

(Step S804)

The action assistance unit 106 assists with the rise action of the user. Note that in FIG. 8, the detector circuit 105 detects whether or not a rise action has started after step S801 (the measurement of the myoelectric potential of the user's lower limbs) and step S802 (the acquisition of the torso angle of the user). This does not mean that the detector circuit 105 detects whether or not a rise action has started after stopping the measurement of the myoelectric potential of the user's lower limbs and the acquisition of the torso angle of the user. Whether or not a rise action has started may be detected while continuing step S801 (the measurement of the myoelectric potential of the user's lower limbs) and step S802 (the acquisition of the torso angle of the user), based on the acquired myoelectric value of the tibialis anterior muscle, the myoelectric value of the vastus lateralis muscle or the vastus medialis muscle, and the torso angle.

(Details of Process of Detecting Start of Rise Action)

Figure 9:
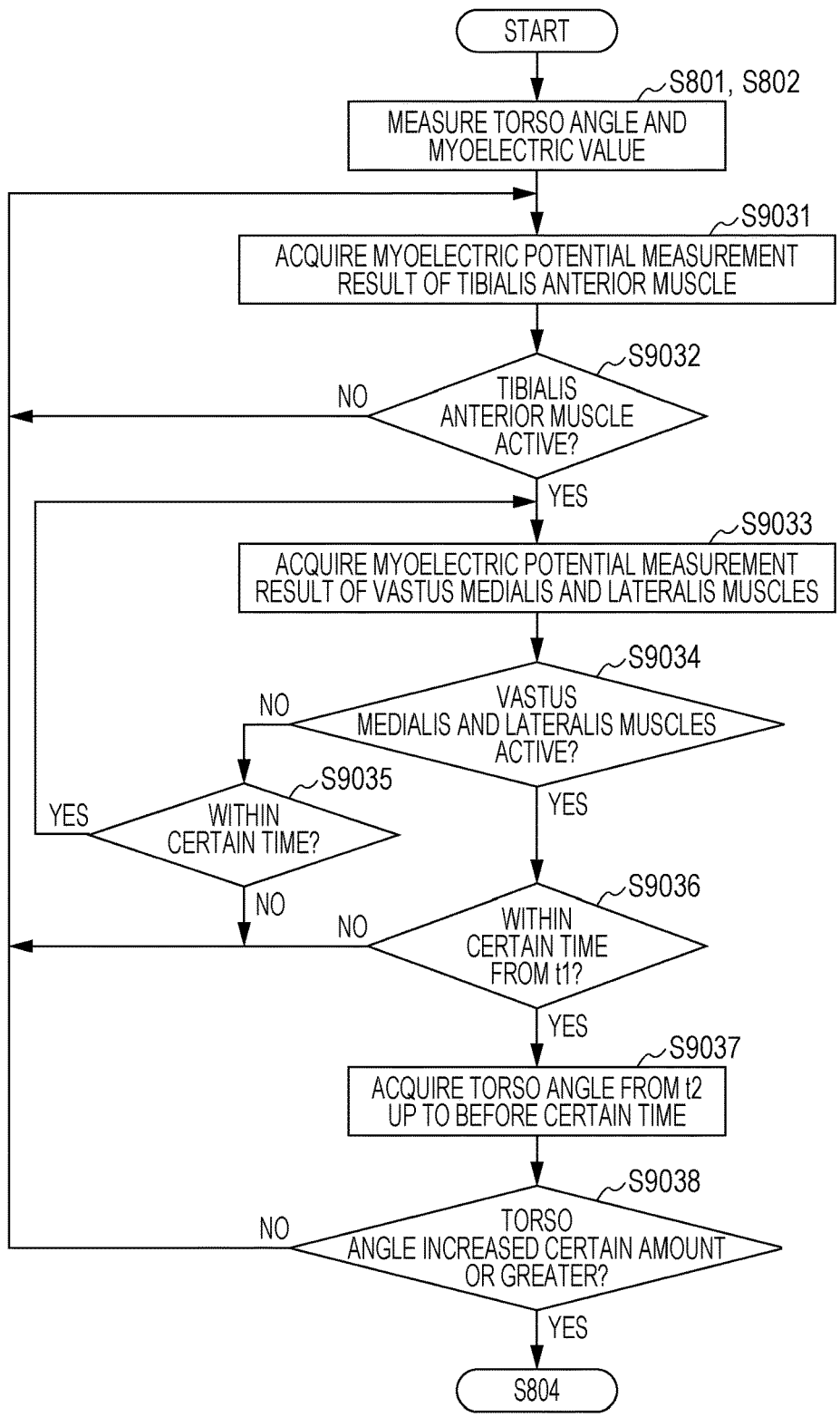
FIG. 9 is a diagram illustrating a detailed flowchart of a rise action detector circuit.

FIG. 9 illustrates a more detailed flowchart of step S803.

(Step S9031)

The detector circuit 105 acquires the myoelectric value of the tibialis anterior muscle.

(Step S9032)

The detector circuit 105 detects whether or not the myoelectric value of the tibialis anterior muscle is equal to or greater than a first threshold value (th1). A myoelectric value of the tibialis anterior muscle equal to or greater than the first threshold value indicates that the tibialis anterior muscle is active.

If the myoelectric value of the tibialis anterior muscle is equal to or greater than the first threshold value (i.e., if the tibialis anterior muscle is active), the process proceeds to step S9033. If the myoelectric value of the tibialis anterior muscle is less than the first threshold value, the process returns to step S9031. Note that this means that after returning to step S9031, a new myoelectric value of the tibialis anterior muscle is acquired.

Note that the detector circuit 105 may also make a judgment based not on an absolute value of the myoelectric value of the tibialis anterior muscle, but on a value of the change in the myoelectric value of the tibialis anterior muscle. For example, the detector circuit 105 may take tb to be the time at which the myoelectric potential is measured when sensing that the change in the activity value of the tibialis anterior muscle is equal to or greater than the first threshold value, and store tb in the measurement data storage unit 104. Herein, tb is taken to be the time at which lb is measured when the change in the myoelectric value of the tibialis anterior muscle (lb-la) is equal to or greater than the first threshold value. Note that ta and tb are taken to be times (where ta<tb), la is taken to be the myoelectric value measured at time ta, and lb is taken to be the myoelectric value measured at time tb (when equal to or greater than the first threshold value, lb>la).

(Step S9033)

The detector circuit 105 acquires the myoelectric value of the vastus muscle.

(Step S9034)

The detector circuit 105 detects whether or not the myoelectric value of the vastus muscle is equal to or greater than a second threshold value (th2). A myoelectric value of the vastus medialis muscle or a myoelectric value of the vastus lateralis muscle equal to or greater than the second threshold value indicates that the vastus medialis or lateralis muscle is active.

If the myoelectric value of the vastus muscle is equal to or greater than the second threshold value, the process proceeds to step S307. If the myoelectric value of the vastus muscle is less than the second threshold value, the process returns to step S306.

Note that the detector circuit 105 may also make a judgment based not on an absolute value of the myoelectric value of the vastus medialis or lateralis muscle, but on a value of the change in the myoelectric value of the vastus medialis or lateralis muscle. For example, the detector circuit 105 may take td to be the time at which the myoelectric potential is measured when sensing that the change in the activity value of the vastus medialis or lateralis muscle is equal to or greater than the second threshold value, and store td in the measurement data storage unit 104. Herein, td is taken to be the time at which ld is measured when the change in the myoelectric value of the vastus medialis or lateralis muscle (ld-lc) is equal to or greater than the second threshold value. Note that tc and td are taken to be times (where tc<td), ld is taken to be the myoelectric value measured at time td, and lc is taken to be the myoelectric value measured at time tc (when equal to or greater than the second threshold value, ld>lc).

(Step S9035)

The detector circuit 105 determines whether or not the time at which the acquired myoelectric value of the tibialis anterior muscle is measured is within a certain amount of time from the time at which a myoelectric value of the tibialis anterior muscle equal to or greater than the first threshold value is measured (that is, within a certain amount of time from t1). If within the certain amount of time, the process returns to step S9033. If greater than the certain amount of time, the process returns to step S9031.

(Step S9035)

The detector circuit 105 determines whether or not the amount of time from t1 to the current time is equal to or greater than the certain amount of time. If the amount of time from t1 to the current time is within the certain amount of time DT, the process returns to step S9033, and the myoelectric value of the vastus muscle is acquired. If the amount of time from t1 to the current time is greater than the certain amount of time DT, the process returns to step S9031.

(Step S9036)

In step S9036, it is determined whether or not a time t2 at which the vastus muscle is determined to be active in step S9034 is within a certain amount of time DT from the time t1, and if within the certain amount of time DT, the process proceeds to step S9037, whereas if the certain amount of time DT has elapsed, the process returns to step S9031.

(Step S9037)

The torso angle from the time t2 at which the vastus muscle is determined to be active in step S9034 up until a time t3 before the certain amount of time (DT2) is acquired.

(Step S9038)

The detector circuit 105 compares the values of the two points of the torso angle at time t2 and the torso angle at time t3 acquired in step S9037, and determines whether or not the torso angle has increased (forward bend posture) from time t2 to time t3. If the torso angle has not increased from time t2 to time t3, the recorded times t1, t2, and t3 are cleared, and the process returns to step S9031. If the torso angle has increased by a certain value or greater from time t2 to time t3, the process proceeds to step S804.

In addition, a threshold value may be set for the increase value of the torso angle. For example, if the torso angle increases by an amount equal to or greater than the threshold value from time t2 to time t3, the process proceeds to step S804. If the torso angle increases from time t2 to time t3, but the amount of increase is within the threshold value, the process returns to step S9031.

In addition, the torso angle from time t2 to time t3 may be partitioned by a time window dt, and the process may be configured to proceed to step S804 only when the mean value of the torso angle increases successively in each window from time t2 to time t3. Note that although the detector circuit 105 acquires the myoelectric value of the vastus muscle after step S9032, the process is not limited thereto, and the detector circuit 105 may also acquire the myoelectric value of the vastus muscle at the same time as step S9031.

(Modifications)

Figure 14:
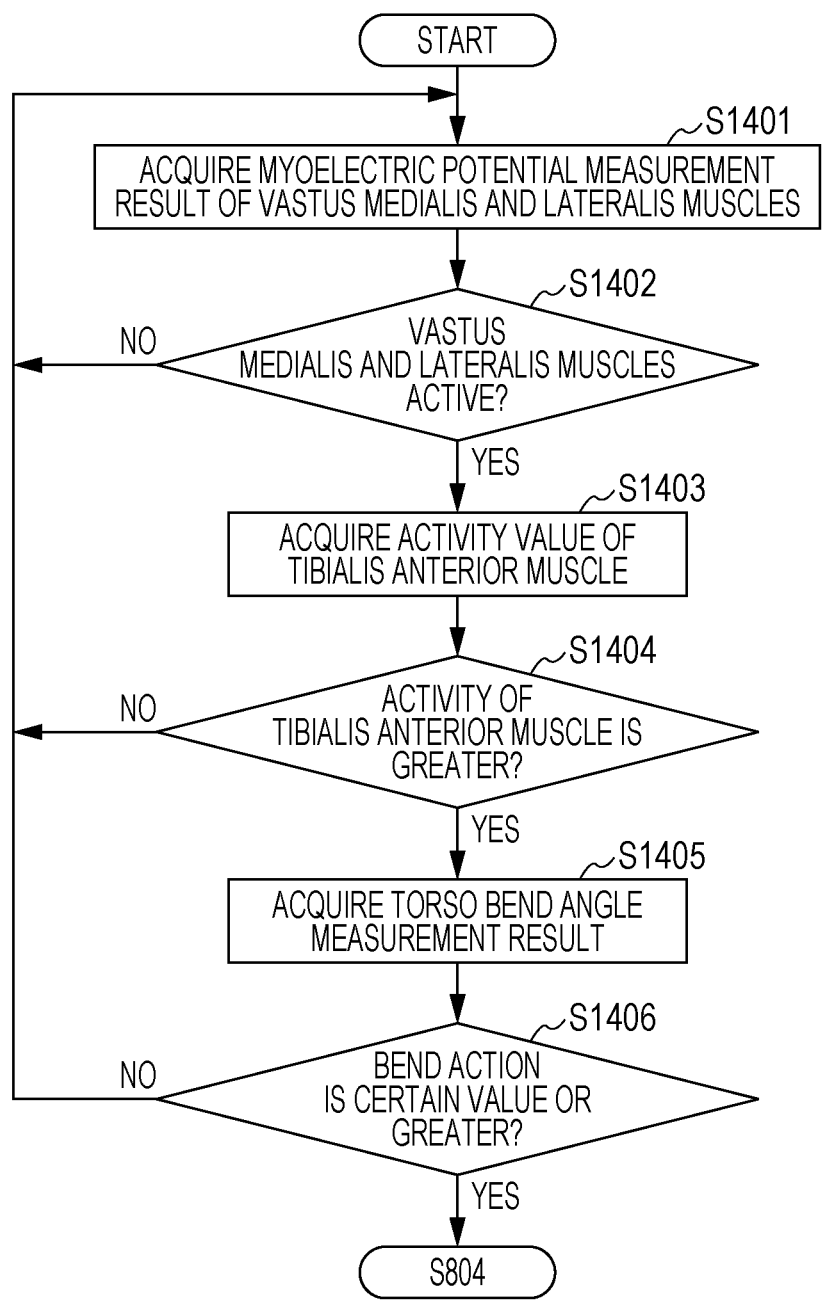
FIG. 14 is a diagram illustrating a detailed flowchart of a rise action detector circuit.

FIG. 14 illustrates a modification of the process flowchart for step S803. Before step S1401 illustrated in FIG. 14, step S801 and step S802 are executed, and after step S1406, step S804 is executed.

(Step S1401)

The detector circuit 105 acquires the myoelectric value of the vastus muscle from the myoelectric potential measurement unit 101.

(Step S1402)

The detector circuit 105 detects whether or not the myoelectric value of the vastus muscle is equal to or greater than a third threshold value (th3). A myoelectric value of the vastus muscle equal to or greater than the third threshold value indicates that the vastus medialis muscle or the vastus lateralis muscle is active.

If the myoelectric value of the vastus muscle is equal to or greater than the third threshold value, the time (t4) at which the myoelectric potential is measured when sensing that the change in the activity value of the vastus muscle is equal to or greater than the third threshold value is stored in the measurement data storage unit 104, and the process proceeds to step S1403. If the myoelectric value of the vastus muscle is less than the third threshold value, the process returns to step S1401.

Note that, similarly to the above embodiment, the detector circuit 105 may also make a judgment based not on an absolute value of the myoelectric value of the vastus muscle, but on a value of the change in the myoelectric value of the vastus medialis or lateralis muscle.

(Step S1403)

The detector circuit 105 acquires from the myoelectric potential measurement unit 101 the myoelectric value at time t4 from the myoelectric measurement value of the tibialis anterior muscle at time t4.

(Step S1404)

The detector circuit 105 compares the myoelectric value of the tibialis anterior muscle at time t4 to the myoelectric value of the vastus muscle at time t4, and determines whether or not the myoelectric value of the tibialis anterior muscle is equal to or greater than the myoelectric value of the vastus muscle. A myoelectric value of the tibialis anterior muscle equal to or greater than the myoelectric value of the vastus muscle indicates that the tibialis anterior muscle is active before the vastus muscle. If the myoelectric value of the tibialis anterior muscle is equal to or greater than the myoelectric value of the vastus muscle, the process proceeds to step S1405. If the myoelectric value of the tibialis anterior muscle is not equal to or greater than the myoelectric value of the vastus muscle, the process returns to step S1401.

(Step S1405)

The detector circuit 105 acquires the torso angle at the time t4 at which the vastus muscle is determined to be active in step S1402, and the torso angle at a time t5 before a certain amount of time (DT3) from time t4.

(Step S1406)

The detector circuit 105 compares the values of the two points of the torso angle at time t4 and the torso angle at time t5 acquired in step S1405, and determines whether or not the torso angle at time t4 is greater than the torso angle at time t5, or in other words, whether or not the torso angle has increased (forward bend posture). If the torso angle has not increased from time t4 to time t5, the recorded times t4 and t5 are cleared, and the process returns to step S1401. If the torso angle has increased from time t4 to time t5, the process proceeds to step S804.

In the present disclosure, all or part of a unit, device, member, or section, or all or part of the function blocks in the block diagram illustrated in FIG. 1, may also be executed by one or multiple electronic circuits, including a semiconductor device, a semiconductor integrated circuit (IC), or a large-scale integration (LSI) chip. An LSI chip or IC may be integrated into a single chip, or be configured by combining multiple chips. For example, function blocks other than storage elements may be integrated into a single chip. Although referred to as an LSI chip or IC herein, such electronic circuits may also be called a system LSI chip, a very large-scale integration (VLSI) chip, or an ultra large-scale integration (ULSI) chip, depending on the degree of integration. A field-programmable gate array (FPGA) programmed after fabrication of the LSI chip, or a reconfigurable logic device in which interconnection relationships inside the LSI chip may be reconfigured or in which circuit demarcations inside the LSI chip may be set up, may also be used for the same purpose.

Furthermore, the function or operation of all or part of a unit, device, member, or section may also be executed by software processing. In this case, the software is recorded onto a non-transitory recording medium, such as one or multiple ROM modules, optical discs, or hard disk drives, and when the software is executed by a processor, the function specified by the software is executed by the processor and peripheral devices. A system or device may also be equipped with one or multiple non-transitory recording media on which the software is recorded, a processor, and necessary hardware devices, such as an interface, for example.

(Embodiment 2)

Figure 16:
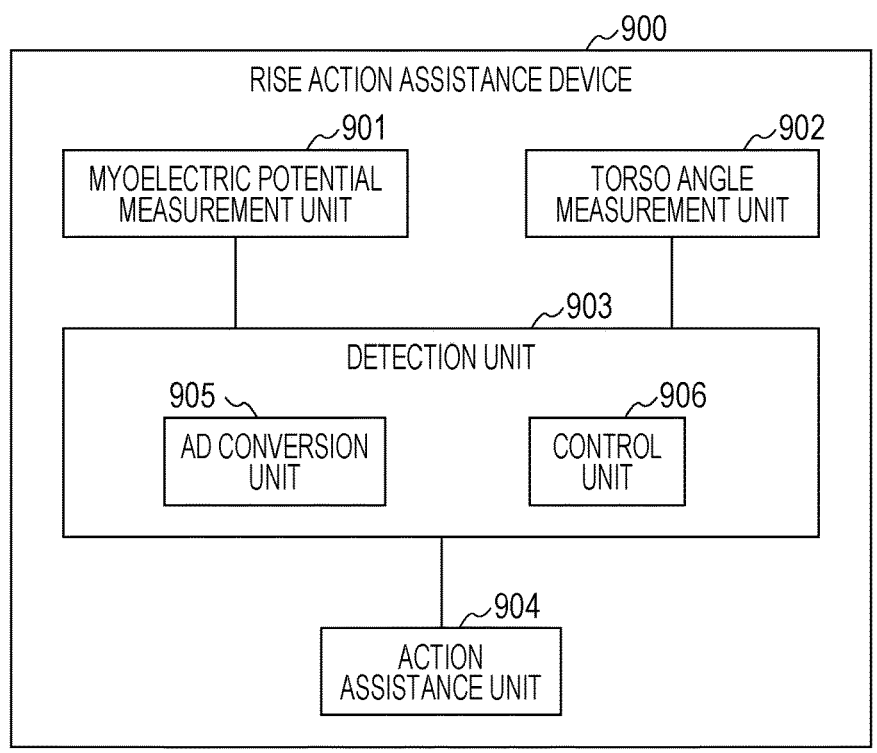
FIG. 16 is a diagram illustrating function blocks of a rise action assistance device.

FIG. 16 is a function block diagram of a rise action assistance device 900 according to an aspect of the present disclosure. The rise action assistance device 900 illustrated in FIG. 16 is equipped with a myoelectric potential measurement unit 901, a torso angle measurement unit 902, a detection unit 903, and an action assistance unit 904. The detection unit 903 includes an analog/digital (AD) conversion unit 905 and a control unit 906. Hereinafter, each of these structural elements will be described.

(Myoelectric Potential Measurement Unit 901)

The myoelectric potential measurement unit 901 includes multiple measurement units. The multiple measurement units includes a first measurement unit, a second measurement unit, and a third measurement unit. Each of the first measurement unit, the second measurement unit, and the third measurement unit includes a pair of electrodes. The respective electrodes are placed at certain sites on the user's body.

The pair of electrodes included in the first measurement unit is placed at a certain site on the skin over the user's tibialis anterior muscle. The pair of electrodes included in the second measurement unit is placed at a certain site on the skin over the user's vastus lateralis muscle. The pair of electrodes included in the third measurement unit is placed at a certain site on the skin over the user's vastus medialis muscle. The first measurement unit uses the pair of electrodes included in the first measurement unit to measure a myoelectric potential value of the tibialis anterior muscle. The second measurement unit uses the pair of electrodes included in the second measurement unit to measure a myoelectric potential value of the vastus lateralis muscle. The third measurement unit uses the pair of electrodes included in the third measurement unit to measure a myoelectric potential value of the vastus medialis muscle.

It is sufficient for the certain site on the skin over the tibialis anterior muscle, the certain site on the skin over the vastus lateralis muscle, and the certain site on the skin over the vastus medialis muscle to be sites at which the S/N ratios of the respective myoelectric potential values satisfy design values. Each of the first measurement unit, the second measurement unit, and the third measurement unit includes a myoelectric potential measurement circuit that is electrically connected to the pair of electrodes discussed above. The myoelectric potential measurement circuit includes a differential amplifier circuit, a full-wave rectifier circuit, and a filter circuit.

The process conducted by the first measurement unit is described below. The output signals from the pair of electrodes are input into the differential amplifier circuit, and the differential amplifier circuit amplifies and outputs the difference between the input signals. The output signal from the differential amplifier circuit is input into the full-wave rectifier circuit, and the full-wave rectifier circuit performs full-wave rectification on the input signal and outputs the result. The output signal from the full-wave rectifier circuit is input into the filter circuit, and the filter circuit outputs a signal including frequencies from 2 Hz to 5 Hz, for example, from among the input signal. The output signal from the filter circuit is the output signal of the myoelectric potential measurement circuit. The first measurement unit treats the output signal from the myoelectric potential measurement circuit included in the first measurement unit as a first output signal, and outputs the first output signal to the detection unit 903 wirelessly, for example.

The above thus describes the process conducted by the first measurement unit. The processes conducted by the second measurement unit and the third measurement unit are similar to the process conducted by the first measurement unit described above. The second measurement unit outputs the output signal from the myoelectric potential measurement circuit included in the second measurement unit as a second output signal. The third measurement unit outputs the output signal from the myoelectric potential measurement circuit included in the third measurement unit as a third output signal. The myoelectric potential measurement unit 901 outputs the first output signal, the second output signal, and the third output signal.

(Torso Angle Measurement Unit 902)

The torso angle measurement unit 902 is placed on the user's lower back, similar to the torso angular velocity sensor 601 in FIG. 6A. The torso angle measurement unit 902 includes an angular velocity sensor that detects the angular velocity in the y-axis direction described in Embodiment 1, and an integrating circuit that integrates the measurement values from the angular velocity sensor. The torso angle measurement unit 902 outputs the output signal from the integrating circuit to the detection unit 903 wirelessly as a fourth output signal, for example. The fourth output signal is a signal indicating the degree of the user's forward bend. As the output signal becomes larger, the degree of the user's forward bend increases (the angle between the user's upper body and the horizontal plane becomes smaller).

(Detection unit 903)

The detection unit 903 includes the AD conversion unit 905 and the control unit 906. The AD conversion unit 905 includes multiple AD converters. The multiple AD converters include a first AD converter, a second AD converter, a third AD converter, and a fourth AD converter. The first AD converter AD converts the first output signal at a certain timing, and outputs a first output value. The second AD converter AD converts the second output signal at a certain timing, and outputs a second output value. The third AD converter AD converts the third output signal at a certain timing, and outputs a third output value. The fourth AD converter AD converts the fourth output signal at a certain timing, and outputs a fourth output value. Note that instead of four AD converters, the AD conversion unit 905 may be made up of a single AD converter and a multiplexer that selectively switches among the first output signal, the second output signal, the third output signal, and the fourth output signal.

The control unit 906 uses the first output value that varies according to the variation in the myoelectric potential value of the tibialis anterior muscle, the second output value that varies according to the variation in the myoelectric potential value of the vastus lateralis muscle, the third output value that varies according to the variation in the myoelectric potential value of the vastus medialis muscle, and fourth output value that varies according to the degree of the user's forward bend to conduct a certain process, and if a condition is satisfied, outputs a first detection signal. The output of the first detection signal indicates that the user's intent to rise has been detected. Note that this certain process will be discussed later.

(Action Assistance Unit 904)

The action assistance unit 904 receives the first detection signal, and starts assisting with the user's rise action. The action assistance unit 904 is described as the action assistance unit 106 in Embodiment 1. Note that the upper skeleton unit 1061 indicated in Embodiment 1 may be construed as an upper leg support unit that supports the user's upper legs or a portion thereof, while the lower skeleton unit 1062 indicated in Embodiment 1 may be construed as a lower leg support unit that supports the user's lower legs or a portion thereof.

The detection unit 903 may also be integrated with the power unit (1063 illustrated in FIG. 7) included in the action assistance unit 904, and the detection unit 903 and the torso angle measurement unit 902 may also exchange signals wirelessly.

(Process of Control Unit 906)

Figure 17:
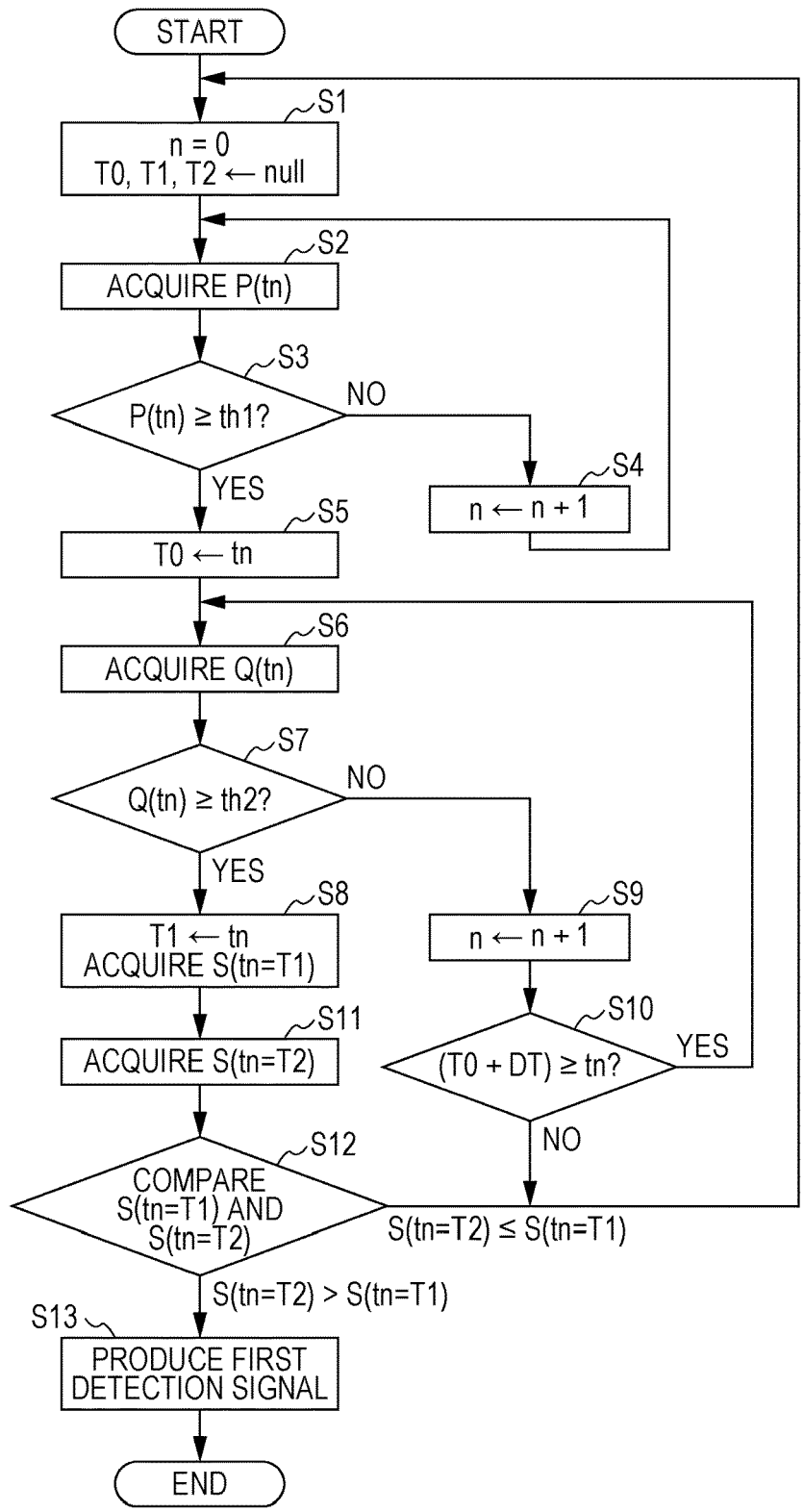
FIG. 17 is a diagram illustrating a flowchart of a process conducted by a control unit.

FIG. 17 is a flowchart of a process conducted by the control unit 906. Before describing the flowchart, the first output value, the second output value, the third output value, and the fourth output value used in the process conducted by the control unit 906 will be described below.

The instantaneous value of the first output signal, the instantaneous value of the second output signal, the instantaneous value of the third output signal, and the instantaneous value of the fourth output signal respectively vary over time. The control unit 906 controls the timing of the AD conversion of the first AD converter. As a result, the first AD converter outputs the first output value updated every time a certain amount of time elapses. The control unit 906 controls the timing of the AD conversion of the second AD converter. As a result, the second AD converter outputs the second output value updated every time a certain amount of time elapses. The control unit 906 controls the timing of the AD conversion of the third AD converter. As a result, the third AD converter outputs the third output value updated every time a certain amount of time elapses. The control unit 906 controls the timing of the AD conversion of the fourth AD converter. As a result, the fourth AD converter outputs the fourth output value updated every time a certain amount of time elapses. The process conducted by the control unit 906 uses the first output value, the second output value, the third output value, and the fourth output value which are updated every time a certain amount of time elapses in this way.

Note that the control unit 906 may also produce an interrupt process, which is a different process from the process illustrated in FIG. 17, activate each of the AD converters, read out the output values from the AD converters, and record the readout values to memory included in the control unit 906 (not illustrated; hereinafter designated control unit memory). It is sufficient to use the values read out and recorded in this way as the first output value, the second output value, the third output value, and the fourth output value used in the process illustrated in FIG. 17 or the like.

Note that if P(tn, n=i) is the first output value of the first AD converter obtained by the ith activation of the first AD converter, P(tn, n=i+1) may be the first output value of the first AD converter obtained by the (i+1)th activation of the first AD converter. The relationship between Q(tn, n=i) and Q(tn, n=i+1), the relationship between R(tn, n=i) and R(tn, n=i+1), and the relationship between S(tn, n=i) and S(tn, n=i+1) are likewise the same as the relationship between P(tn, n=i) and P(tn, n=i+1) described above. The time interval between the time tn (n=i) and the time tn (n=i+1) depends on the activation timing of the AD converter.

Note that the AD conversion timing of the first AD converter, the AD conversion timing of the second AD converter, the AD conversion timing of the third AD converter, and the AD conversion timing of the fourth AD converter may also be synchronized.

The above thus describes the first output value, the second output value, the third output value, and the fourth output value used in the process conducted by the control unit 906.

(Step S1)

The control unit 906 sets the time tn to n=0. The time tn (n=0) may also be taken to be the time 0. T0, T1, and T2 recorded in the control unit memory are set to null values. T0, T1, and T2 will be discussed later. Note that the time interval between tn (n=i, where i is 0 or a natural number) and tn (n=i+1) may be decided according to the design specifications of the output value sampling interval, including factors such as the time in which the AD converter is able to update the output value as discussed above.

(Step S2)

The control unit 906 references the control unit memory, and acquires P(tn), which is the first output value at the time tn.

(Step S3)

The control unit 906 detects whether or not P(tn) is equal to or greater than a first threshold value th1. If P(tn) is equal to or greater than the first threshold value, the process proceeds to step S5. If P(tn) is less than the first threshold value, n is set to n=n+1 in step S4, and then the process returns to step S2. Note that returning to step S2 means that a new P(tn) is acquired after a certain amount of time elapses.

(Step S5)

The control unit 906 records the time tn at which P(tn) becomes equal to or greater than the first threshold value in the control unit memory as T0.

(Step S6)

The control unit 906 references the control unit memory, and acquires Q(tn), which is the second output value at the time tn.

(Step S7)

The control unit 906 detects whether or not Q(tn) is equal to or greater than a second threshold value th2. If Q(tn) is equal to or greater than th2, the process proceeds to step S8. If Q(tn) is less than th2, n is set to n=n+1 in step S9, and the process proceeds to step S10.

(Step S10)

The control unit 906 references T0 recorded in the control unit memory, and determines whether or not the time tn is within a certain amount of time DT from T0. If the time tn is within the certain amount of time DT from T0, the process returns to step S6. Note that returning to step S6 means that a new Q(tn) is acquired after a certain amount of time elapses. If greater than the certain amount of time, the process returns to step S1.

(Step S8)

The control unit 906 records the time tn at which Q(tn) becomes equal to or greater than th2 in the control unit memory as T1. The control unit 906 references the control unit memory, acquires and records in the control unit memory S(tn=T1), which is the fourth output value at the time tn.

(Step S11)

The control unit 906 waits until a certain amount of time elapses from the time T1, and when tn=T2, the control unit 906 references the control unit memory, and acquires S(tn=T2), which is the fourth output value at the time tn=T2. Herein, T2=(T1+a certain amount of time).
(Step S12)

The control unit 906 compares S(tn=T1) and S(tn=T2) recorded in the control unit memory, and determines whether or not the torso angle has increased (forward bend posture). If the torso angle has not increased from time T1 to time T2, the process returns to step S1. If the torso angle has increased by a certain value or greater from time T1 to time T2, the process proceeds to step S13.
(Step S13)

The control unit 906 sends the first detection signal to the action assistance unit 904.

The above thus describes a flowchart of the process conducted by the control unit 906.
(Second Output Value and Third Output Value)

Note that the above describes using Q(tn) without using the third output value of R(tn). In this case, the third measurement unit and the third AD converter are unnecessary.

Also, the above describes using Q(tn), but the third output value of R(tn) may also be used instead of Q(tn). In this case, the second measurement unit and the second AD converter are unnecessary.

Furthermore, the above describes using Q(tn), but both Q(tn) and R(tn) may also be used. For this case, changes to the flowchart in FIG. 17 are listed below.

(Step S6): Change "The control unit 906 references the control unit memory, and acquires Q(tn), which is the second output value at the time tn." to "The control unit 906 references the control unit memory, and acquires Q(tn), which is the second output value at the time tn, and R(tn), which is the third output value at the time tn."

(Step S7): Change "The control unit 906 detects whether or not Q(tn) is equal to or greater than a second threshold value th2. If Q(tn) is equal to or greater than th2, the process proceeds to step S8. If Q(tn) is less than th2, n is set to n=n+1 in step S9, and the process proceeds to step S10." to "The control unit 906 detects whether or not Q(tn) is equal to or greater than a second threshold value th2 and also R(tn) is equal to or greater than the second threshold value th2. If Q(tn) is equal to or greater than th2 and also R(tn) is equal to or greater than th2, the process proceeds to step S8. Otherwise, that is, if at least one of Q(tn) and R(tn) is less than th2, n is set to n=n+1 in step S9, and the process proceeds to step S10."

(Step S8): Change "The control unit 906 records the time tn at which Q(tn) becomes equal to or greater than th2 in the control unit memory as T1. The control unit 906 acquires and records in the control unit memory S(tn=T1), which is the fourth output value at the time tn." to "The control unit 906 records the time tn at which Q(tn) and R(tn) become equal to or greater than th2 in the control unit memory as T1. The control unit 906 acquires and records in the control unit memory S(tn=T1), which is the fourth output value at the time tn.

(AD Conversion Unit)

In addition, the detection unit 903 may also not include the AD conversion unit 905, while the myoelectric potential measurement unit 901 may include the first AD converter, the second AD converter, and the third AD converter, and the torso angle measurement unit 902 may include the fourth AD converter.

In this case, the AD conversion timings of the first AD converter, the second AD converter, the third AD converter, and the fourth AD converter may be specified not by receiving instructions from the control unit 906, but instead, AD conversion may be performed every time respective predetermined amounts of time elapse.

In this case, the myoelectric potential measurement unit 901 may also send the AD-converted first output value instead of the first output signal, the AD-converted second output value instead of the second output signal, and the AD-converted third output value instead of the third output signal to the control unit 906 wirelessly. The first output value, the second output value, and the third output value received by the control unit 906 may be held in the control unit memory. The control unit 906 may also use the data held in the control unit memory in step S2 and step S6.

In this case, the torso angle measurement unit 902 may also send the AD-converted fourth output value instead of the fourth output signal to the control unit 906 wirelessly. The fourth output value received by the control unit 906 may be held in the control unit memory. The control unit 906 may also use the data held in the control unit memory in step S8 and step S11.

In this case, the AD conversion timings of the first AD converter, the second AD converter, the third AD converter, and the fourth AD converter may be specified not by receiving instructions from the control unit 906, but instead, AD conversion may be performed every time respective predetermined amounts of time elapse.

The foregoing thus describes a rise action assistance device according to one or more aspects on the basis of the embodiments, but the present disclosure is not limited to these embodiments. Embodiments obtained by applying various modifications that may occur to persons skilled in the art as well as embodiments constructed by combining the structural elements in different embodiments may also be included within the scope of the one or more exemplary embodiments insofar as such embodiments do not depart from the spirit of the present disclosure.

In the present disclosure, all or part of the units and devices, or all or part of the function blocks in the block diagrams illustrated in FIGS. 1, 2, and 16, may also be executed by one or multiple electronic circuits, including a semiconductor device, a semiconductor integrated circuit (IC), or a large-scale integration (LSI) chip. An LSI chip or IC may be integrated into a single chip, or be configured by combining multiple chips. For example, function blocks other than storage elements may be integrated into a single chip. Although referred to as an LSI chip or IC herein, such electronic circuits may also be called a system LSI chip, a very large-scale integration (VLSI) chip, or an ultra large-scale integration (ULSI) chip, depending on the degree of integration. A field-programmable gate array (FPGA) programmed after fabrication of the LSI chip, or a reconfigurable logic device in which interconnection relationships inside the LSI chip may be reconfigured or in which circuit demarcations inside the LSI chip may be set up, may also be used for the same purpose.

Furthermore, the function or operation of all or part of a unit, device, or part of a device may also be executed by software processing. In this case, the software is recorded onto a non-transitory recording medium, such as one or multiple ROM modules, optical discs, or hard disk drives, and when the software is executed by a processor, the software causes the processor and peripheral devices to execute specific functions in software. A system or device may also be equipped with one or multiple non-transitory recording media on which the software is recorded, a processor, and necessary hardware devices, such as an interface, for example.

Also, in the above embodiments, each structural element may be configured by dedicated hardware, or realized by executing a software program suited to each structural element. Each structural element may be realized as a result of a program execution unit such as a CPU or processor reading out and executing a software program recorded on a recording medium such as a hard disk or semiconductor memory. Herein, software realizing a rise action assistance device of the foregoing embodiments is a program causing a computer to execute each step included in the flowcharts illustrated in FIGS. 8, 9, 14, and 17, for example.

A rise action assistance device according to the present disclosure is applicable to users requiring rise assistance.

What is claimed is:

1. A rise action assistance device, comprising:
   a myoelectric potential acquirer that acquires a myoelectric value of a sitting user's tibialis anterior muscle, and at least one of a myoelectric value of the sitting user's vastus lateralis muscle and a myoelectric value of the sitting user's vastus medialis muscle;
   an angle acquirer that acquires a bend angle of the sitting user's upper body;
   a detector circuit that detects a start of a rise action by the user, based on the myoelectric value of the user's tibialis anterior muscle, at least one of the myoelectric value of the user's vastus lateralis muscle and the myoelectric value of the user's vastus medialis muscle, and the bend angle of the user's upper body; and
   an assistor that starts assistance of the rise action after the detector circuit detects the start of the rise action, wherein
   the detector circuit detects that the sitting user has started the rise action when
   (a) the myoelectric value of the user's tibialis anterior muscle acquired by the myoelectric potential acquirer within a first certain amount of time is equal to or greater than a first threshold value,
   (b) at least one of the myoelectric value of the user's vastus lateralis muscle and the myoelectric value of the user's vastus medialis muscle acquired by the myoelectric potential acquirer within the first certain amount of time is equal to or greater than a second threshold value, and
   (c) the bend angle of the user's upper body acquired by the angle acquirer within the first certain amount of time is increasing.

2. The rise action assistance device according to claim 1, wherein
   the detector circuit detects that a time point at which (a) to (c) are satisfied is before a second certain amount of time from a start point of the sitting user's rise action.

3. The rise action assistance device according to claim 1, wherein
   the assistor assists with the rise action by the user within a third certain amount of time after the detector circuit detects the start of the rise action.

4. A rise action assistance device, comprising:
   a myoelectric potential acquirer that acquires a myoelectric value of a sitting user's tibialis anterior muscle, and at least one of a myoelectric value of the sitting user's vastus lateralis muscle and a myoelectric value of the sitting user's vastus medialis muscle;
   an angle acquirer that acquires a bend angle of the sitting user's upper body;
   a detector circuit that detects a start of a rise action by the user, based on the myoelectric value of the user's tibialis anterior muscle, at least one of the myoelectric value of the user's vastus lateralis muscle and the myoelectric value of the user's vastus medialis muscle, and the bend angle of the user's upper body; and
   an assistor that starts assistance of the rise action after the detector circuit detects the start of the rise action, wherein
   the detector circuit detects that the user has started the rise action when
   (a) the detector circuit detects that the myoelectric value of the user's tibialis anterior muscle is equal to or greater than a first threshold value,
   (b) the detector circuit, after detecting that the myoelectric value of the user's tibialis anterior muscle is equal to or greater than the first threshold value, detects that the myoelectric value of the user's vastus lateralis muscle or vastus medialis muscle is equal to or greater than a second threshold value, and
   (c) the detector circuit detects that the bend angle of the user's upper body is increasing in a period after detecting that the myoelectric value of the user's tibialis anterior muscle is equal to or greater than the first threshold value until detecting that the myoelectric value of the user's vastus lateralis muscle or vastus medialis muscle is equal to or greater than the second threshold value.

5. A rise action assistance method, comprising:
   acquiring a myoelectric value of a sitting user's tibialis anterior muscle, and at least one of a myoelectric value of the sitting user's vastus lateralis muscle and a myoelectric value of the sitting user's vastus medialis muscle;
   acquiring a bend angle of the sitting user's upper body;
   detecting a start of a rise action by the user, based on the myoelectric value of the user's tibialis anterior muscle, at least one of the myoelectric value of the user's vastus lateralis muscle and the myoelectric value of the user's vastus medialis muscle, and the bend angle of the user's upper body; and
   starting assistance of the rise action after detecting the start of the rise action, wherein
   the start of the rise action by the sitting user is detected when
   (a) the myoelectric value of the user's tibialis anterior muscle acquired within a first certain amount of time is equal to or greater than a first threshold value,
   (b) at least one of the myoelectric value of the user's vastus lateralis muscle and the myoelectric value of the user's vastus medialis muscle acquired within the first certain amount of time is equal to or greater than a second threshold value, and
   (c) the bend angle of the user's upper body acquired within the first certain amount of time is increasing.

6. An assistance device, comprising:
   a first myoelectric potential detector that is attached on a first portion of a user to detect a first myoelectric value of a tibialis anterior muscle of the user;
   a second myoelectric potential detector that is attached on a second portion of the user to detect a second myoelectric value of a vastus lateralis muscle of the user or a vastus medialis muscle of the user;
   an angle detector that detects a bend angle of an upper body of the user; and
   an assistor that starts assisting the user to rise based on the first myoelectric value and the second myoelectric value, both the first myoelectric value and the second myoelectric value being detected during increasing of the bend angle.

* * * * *